(12) United States Patent
Machhammer et al.

(10) Patent No.: US 6,350,906 B2
(45) Date of Patent: *Feb. 26, 2002

(54) CONTINUOUS RECOVERY OF (METH)ACRYLIC ACID

(75) Inventors: Otto Machhammer, Mannheim; Peter Zehner, Ludwigshafen, both of (DE); Filip Deberdt, Muinzen (BE)

(73) Assignee: BASF Aktiengesellschaft, Ludwigshafen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 57 days.

(21) Appl. No.: 09/362,912

(22) Filed: Jul. 29, 1999

(30) Foreign Application Priority Data

Aug. 26, 1998 (DE) .......................................... 198 38 795

(51) Int. Cl.⁷ .............................................. C07C 51/42
(52) U.S. Cl. ...................................................... 562/600
(58) Field of Search ........................................... 562/600

(56) References Cited

U.S. PATENT DOCUMENTS

| 3,932,500 A | 1/1976 | Duembgen et al. |
| 4,110,370 A | 8/1978 | Engelbach et al. |
| 5,198,578 A | 3/1993 | Etzkorn et al. |
| 5,218,146 A | 6/1993 | Takata et al. |
| 5,426,221 A | 6/1995 | Willersinn |
| 5,510,558 A | 4/1996 | Umansky et al. |
| 5,705,684 A | 1/1998 | Hefner et al. |
| 5,780,679 A | 7/1998 | Egly et al. |

FOREIGN PATENT DOCUMENTS

| CN | 1105352 | 7/1995 |
| EP | 0 117 146 | 8/1984 |
| EP | 0 706 986 | 4/1996 |
| EP | 706986 A * | 4/1996 |
| FR | 2 756 280 | 5/1998 |

OTHER PUBLICATIONS

F. Cavani, et al., Catalysis Today, vol. 24, pp. 307–313, "The Oxidative Dehydrogenation of Ethane and Propane as an Alternative Way for the Production of Light Olefins," 1995.

* cited by examiner

Primary Examiner—Paul J. Killos
(74) Attorney, Agent, or Firm—Oblon, Spivak, McClelland, Maier & Neustadt, P.C.

(57) ABSTRACT

A process for the continuous recovery of (meth)acrylic acid from the reaction gases of a catalytic gas-phase oxidation by (I) absorption in a high-boiling solvent, (II) isolation of the (meth)acrylic acid from the mixture with the solvent and, if required, further purification of the (meth)acrylic acid isolated, (III) purification of the solvent and (IV) recycling of the purified solvent to absorption stage (I) is proposed, the temperature in each process stage not exceeding 155° C., in particular 140° C., preferably 120° C.

13 Claims, 1 Drawing Sheet

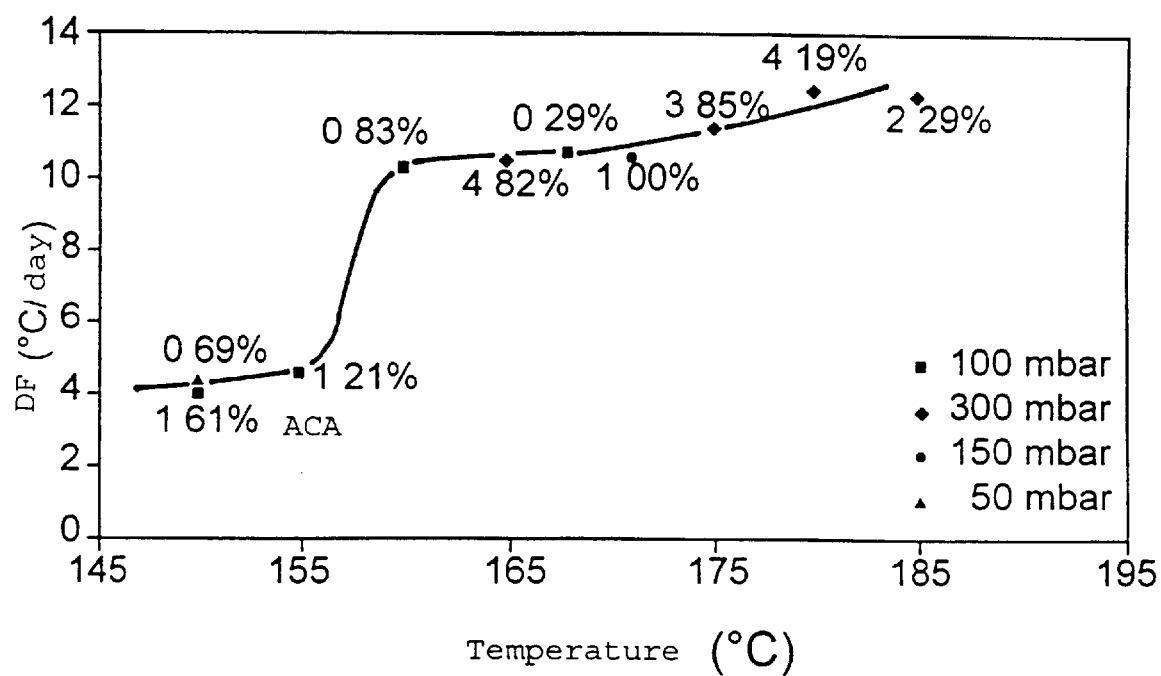

CONTINUOUS RECOVERY OF (METH)ACRYLIC ACID

The present invention relates to a process for the continuous recovery of (meth)acrylic acid by absorption of (meth)acrylic acid from the reaction gases of a catalytic gas-phase oxidation. Below, the term (meth)acrylic acid represents substances acrylic acid and/or methacrylic acid.

(Meth)acrylic acid is prepared predominantly by catalytic gas-phase oxidation of suitable starting materials, in particular of propene and/or acrolein in the case of acrylic acid and of isobutene and/or methacrolein in the case of methacrylic acid.

A number of possibilities are known for isolating the (meth)acrylic acid from the reaction gases of the catalytic gas-phase oxidation, including isolation by absorption in a solvent.

DE-B 21 36 396 discloses the isolation of the acrylic acid from the reaction gases obtained in the catalytic oxidation of propene or acrolein by countercurrent absorption with a mixture of 75% by weight of diphenyl ether and 25% by weight of biphenyl. Furthermore, DE-A 24 49 780 discloses the cooling of the hot reaction gas by partial evaporation of the solvent in a direct condenser (quench apparatus) before the countercurrent absorption. The problem here and in further process steps, in particular in the purification of the (meth)acrylic acid by distillation, is the production of solids in the apparatuses, which reduces the availability of the plant. According to DE-A 43 08 087, this solid fraction can be reduced in the case of acrylic acid by adding a polar solvent, such as dimethyl phthalate, in an amount of from 0.1 to 25% by weight, to the relatively nonpolar solvent mixture comprising diphenyl ether and biphenyl; this increases the absorptivity of the solvent mixture for the contaminants. However, with increasing polarity, the solvent absorbs increasing amounts of water; moreover, this leads to higher solvent losses via the dilute acid solution.

In the presence of solvents, at relatively high temperatures as occur in the recovery of (meth)acrylic acid by the process of the generic type, in particular on the bottom collecting tray of the absorption column, in the stripping section and in the bottom section of the distillation column and in the heat exchangers, the polyacrylic acid forms contamination which adheres firmly to the surface of the apparatuses and can be detached only with alkalis. Analyses have shown that the contamination comprises a mixture of from about 10 to 50% by weight of poly(meth)acrylic acid, the remainder being solvent.

It is an object of the present invention substantially to avoid the susceptibility to soiling in all apparatuses, in particular the production of contamination only soluble in alkali, and hence to improve the availability of the plant and the cost-efficiency of the process for the recovery of (meth) acrylic acid.

We have found that this object is achieved by a process for the continuous recovery of (meth)acrylic acid from the reaction gases originating from a catalytic gas-phase oxidation by (I) absorbing the (meth)acrylic acid in a high-boiling solvent, (II) isolating the (meth)acrylic acid from the mixture with the solvent and, if required, further purifying the (meth)acrylic acid isolated, (III) purifying the solvent and (IV) recycling the purified solvent to absorption stage (I).

In the process, the temperature in each process stage does not exceed 155° C., in particular 140° C., particularly preferably 120° C.

We have found, surprisingly, that the susceptibility to soiling of apparatuses in which a high-boiling solvent and (meth)acrylic acid are used is determined essentially by a process parameter, in particular by the temperature in the apparatuses. The soiling can be substantially avoided if it is ensured that the temperature does not exceed a specific critical value.

On the other hand, the fouling in the apparatuses does not increase, as expected, with increasing (meth)acrylic acid concentration but, on the contrary, the soiling is substantially independent of the (meth)acrylic acid concentration.

The substantial avoidance of soiling by the novel temperature limitation has far-ranging economic consequences: in particular, it is possible to use in the apparatuses elements such as dumped packings or stacked packings which have a greater hydrodynamic load capacity but also higher susceptibility to soiling compared with, for example, dual-flow or valve trays, which are used in the known process for isolating (meth)acrylic acid from mixtures in a high-boiling solvent, owing to their lower susceptibility to soiling. New plants can thus be dimensioned with smaller separation apparatuses, in particular columns, for the same level of production, or the level of production is increased by the novel process in existing plants.

Here, solvents whose boiling point is higher than the boiling point of the respective desired main product (about 141° C. for acrylic acid or about 161° C. for methacrylic acid, in each case at atmospheric pressure) are defined as high-boiling.

Starting mixtures for the present process are the reaction gases from the catalytic gas-phase oxidation of $C_3$-alkanes, $C_3$-alkenes, $C_3$-alkanols and/or $C_3$-alkanals or intermediates for these, to give acrylic acid or of $C_4$-alkanes, $C_3$-alkanes, $C_3$-alkenes, $C_3$-alkanols and/or $C_3$-alkanals or intermediates for these, to give methacrylic acid. The process is described below for acrylic acid but is it also applicable in an analogous manner for methacrylic acid.

The catalytic gas-phase oxidation of propene and/or acrolein to acrylic acid in air or molecular oxygen by known processes, in particular as described in the abovementioned publications, is particularly advantageous. Temperatures of 200 to 450° C. and, if required, superatmospheric pressure are preferably employed here. The heterogeneous catalysts used are preferably oxidic multicomponent catalysts based on the oxides of molybdenum, bismuth and iron in the 1st stage (oxidation of propene to acrolein) and of the oxides of molybdenum and vanadium in the 2nd stage (oxidation of acrolein to acrylic acid). If propane is used as starting material, it can be converted into a propene/propane mixture by catalytic oxydehydrogenation as described in U.S. Pat. No. 5,510,558 or by homogeneous oxydehydrogenation, as described, for example, in CN-A-1 105 352; or by catalytic dehydrogenation, corresponding to the example in EP-A-0 253 409. When a propene/propane mixture is used, propane acts as a diluent gas. Suitable propene/propane mixtures are also refinery propene (70% of propene and 30% of propane) or cracker propene (95% of propene and 5% of propane). In principle, propene/propane mixtures such as the abovementioned with oxygen or air or a mixture containing oxygen and nitrogen in any composition can be oxidized to acrolein and acrylic acid.

The conversion of propene to acrylic acid is highly exothermic. The reaction gas which, in addition to the starting materials and products, advantageously contains an inert diluent gas, for example recycled gas (see below), atmospheric nitrogen, one or more saturated $C_1$- to $C_6$-hydrocarbons, in particular methane and/or propane, and/or steam can absorb only a small part of the heat of reaction. Although the type of reactor used is not subject to any restriction per se, tube bundle heat exchangers which are cooled by means of a salt bath and are filled with the oxidation catalyst are generally used since the heat evolved in the reaction can be very readily dissipated therein by convection and radiation to the cooled tube walls.

In the case of the catalytic gas-phase oxidation, it is not pure acrylic acid which is obtained but a gaseous mixture which, in addition to the acrylic acid, may contain essentially unconverted acrolein and/or propene, steam, carbon monoxide, carbon dioxide, nitrogen, propane, oxygen, acetic acid, propionic acid, formaldehyde, further acids and aldehydes and maleic anhydride as secondary components. Usually, the reaction product mixture contains from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of the sum of maleic acid and maleic anhydride and from 20 to 90, preferably from 50 to 98, % by weight of inert diluent gases, based in each case on the total reaction mixture. In particular, saturated $C_1$–$C_6$-hydrocarbons, such as from 0 to 95% by weight of methane and/or propane, as well as from 1 to 30% by weight of steam, from 0.05 to 15% by weight of carbon oxides and from 0 to 95% by weight of nitrogen, based in each case on 100% by weight of reaction gas, are present as inert diluent gases.

The process stages for isolating the acrylic acid from the reaction mixture are described below:

Stage I

In stage I, the acrylic acid and a part of the secondary components are absorbed from the reaction gas by absorption in a high-boiling solvent. Preferably, the boiling point of the high-boiling solvent is at least 20° C., in particular 50° C., more preferably 70° C., above the boiling point of the acrylic acid or methacrylic acid. Preferred solvents have boiling points (atmospheric pressure) of from 180 to 400° C., in particular from 220 to 360° C., in the present application the term solvent also including solvent mixtures. Suitable solvents are high-boiling, extremely hydrophobic solvents which contain no externally active polar groups, such as aliphatic or aromatic hydrocarbons, for example middle oil fractions from paraffin distillation, or ethers having bulky groups on the 0 atom, or mixtures thereof, a polar solvent, such as the 1,2-dimethyl phthalate disclosed in DE-A-43 08 087, advantageously being added thereto. Esters of benzoic acid and phthalic acid with straight-chain alkanols of 1 to 8 carbon atoms, such as n-butyl benzoate, methyl benzoate, ethyl benzoate, dimethyl phthalate and diethyl phthalate, and thermal oils, such as biphenyl, diphenyl ether and mixtures of biphenyl and diphenyl ether or their chlorine derivatives and triarylalkanes, e.g. 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane, and mixtures of such isomers are furthermore suitable.

A particularly preferred solvent is a solvent mixture comprising biphenyl and diphenyl ether, preferably in the azeotropic composition, in particular comprising about 25% by weight of biphenyl and about 75% by weight of diphenyl ether, based on 100% by weight of biphenyl and diphenyl ether, for example the commercially available Diphyl®.

This solvent mixture preferably furthermore contains a polar solvent, such as dimethyl phthalate, in an amount of from 0.1 to 25% by weight, based on the total solvent mixture. This reduces the susceptibility of the plants to soiling.

Here, the terms high boilers, medium boilers and low boilers and corresponding adjectives denote, respectively, compounds which have a higher boiling point than acrylic acid (high boilers), those which have about the same boiling point as acrylic acid (medium boilers) and those which have a lower boiling point than acrylic acid (low boilers).

The hot reaction gas is advantageously cooled by partial evaporation of the solvent in a direct condenser or quench apparatus prior to the absorption. Venturi scrubbers, bubble columns or spray condensers are particularly suitable for this purpose. The high-boiling secondary components of the reaction gas condense into the unevaporated solvent. In addition, the partial evaporation of the solvent is a purification step of the solvent. In a preferred embodiment of the invention, a part-stream of the unevaporated solvent, preferably from 1 to 10% of the mass flow fed to the absorption column, is removed and is subjected to a solvent purification. Here, the solvent is distilled over and the high-boiling secondary components remain behind and can be disposed of, e.g. incinerated, if required after further thickening. This solvent distillation serves for avoiding an excessively high concentration of high boilers in the solvent stream. The solvent distilled over is preferably fed to the laden solvent stream from the absorption column.

The absorption takes place in a countercurrent absorption column which is basically equipped with all types of column baffles, preferably with dumped or stacked packings and into which solvent flows from above. The gaseous reaction product and any evaporated solvent from the quench apparatus are passed from below into the column and then cooled to absorption temperatures. The cooling is advantageously effected by cooling loops, i.e. heated solvent is removed from the column, cooled in heat exchangers and fed again to a point above the take-off point of the column. After the absorption, all high boilers, the major part of the acrylic acid and a part of the low boilers are present in the solvent.

The remaining, unabsorbed reaction gas is further cooled in order to separate therefrom the condensable part of the low-boiling secondary components, in particular water, formaldehyde and acetic acid, by condensation. This condensate is referred to below as dilute acid solution. The remaining gas stream predominantly comprises nitrogen, carbon oxides and unconverted starting materials. Some of these are preferably fed back to the reaction stages as diluent gas, referred to below as recycled gas. The atmospheric nitrogen and part of the uncondensed secondary components are removed as waste gas and preferably incinerated.

Stage II

In stage II, the acrylic acid together with the medium boilers and the last residue of low boilers is separated from the solvent.

The isolation of the acrylic acid from the mixture with the solvent is preferably effected by evaporation. The evaporation is carried out at from 10 to 200 mbar and corresponding evaporation temperatures from 60 to 130° C., in particular at from 60 to 100 mbar and from 90 to 110° C. The evaporation gives rise to a vapor stream and a liquid stream. The vapor stream contains the major part of the acrylic acid, i.e. has acrylic acid concentrations of from about 70 to 95%, in particular from about 80 to 90%. The liquid stream from the evaporator contains predominantly the solvent and acrylic acid in a concentration of from about 5 to 15% by weight. This liquid stream must then be purified, preferably, by stripping. The purification of the solvent is described below as process stage (III).

The acrylic acid is purified therefrom in further process steps, for example by distillation or by crystallization.

In a further embodiment, the acrylic acid is isolated by distillation, it being possible in principle to use any distillation column. A column having dual-flow trays is advantageously used for this purpose. In the ascending stripping section of the column, the acrylic acid is freed from the solvent and the medium-boiling secondary components, such as maleic anhydride, by distillation. To reduce the low-boiler fraction in the acrylic acid, the ascending stripping section of the column is advantageously lengthened and the acrylic acid is removed as a side take-off from the column. This acrylic acid is referred to as crude acrylic acid.

A stream rich in low boilers is then taken off at the top of the column after a partial condensation. However, since the stream still contains acrylic acid, it is advantageously not discarded but recycled to absorption stage (I).

From the bottom of the column, a stream, which comprises predominantly solvent, is drawn off and fed to stage III.

In a preferred embodiment of the invention, the dilute acid solution, which may still contain dissolved acrylic acid, is treated by extraction with a small part-stream of the virtually acrylic acid-free solvent (from stage III). The aqueous stream from the extraction with dilute acid solution can be concentrated, which may be necessary in particular if there are environmental requirements.

The crude acrylic acid obtained in stage II contains preferably from 98 to 99.8, in particular from 98.5 to 99.5, % by weight of acrylic acid and from 0.2 to 2, in particular from 0.5 to 1.5, % by weight of impurities, for example acetic acid, aldehydes and maleic anhydride, based in each case on the crude acrylic acid. If its purity requirements are not very high, this acrylic acid may be used as such for esterification.

When process stage II (isolation of the acrylic acid from the mixture with the solvent and any further purification of the acrylic acid isolated) is carried out by distillation, the condition according to the invention, that the temperature in every process stage does not exceed 155° C., in particular 140° C., particularly preferably 120° C., can be realized essentially by two measures: on the one hand by permitting a high acrylic acid concentration in the bottom of the distillation column and on the other hand by reducing the bottom pressure.

In the prior art process, the distillation is operated at a top pressure of about 100 mbar, which, owing to the pressure drop over the column trays, corresponds to a bottom pressure of about 250 mbar and hence to a bottom temperature of about 195° C. and an acrylic acid concentration of about 0.5% by weight in the bottom product.

If an acrylic acid concentration of from 5 to 15, in particular from 8 to 12, % by weight in the bottom product is permitted, it would be possible to maintain a bottom temperature of <155° C. at the same bottom pressure of about 250 mbar and thus dramatically to reduce the degree of fouling.

Owing to the high acrylic acid content of from 8 to 12% by weight, this bottom product cannot be directly recirculated to the absorption column (stage I) but must be purified beforehand, preferably by stripping. The purification of the solvent is described below as process stage III.

At a given composition of the bottom product, the novel temperature limitation to 155° C., in particular 140° C., particularly preferably 120° C., can be achieved by reducing the bottom pressure.

The bottom pressure can be reduced essentially by two measures: by reducing the top pressure of the distillation column and/or by reducing the pressure drop in the column, for example by using suitable column baffles, such as stacked packings. By reducing the top pressure to about 10 mbar, a bottom pressure of from about 170 to 200 mbar can be established. If special column baffles, for example stacked packings, are additionally used, the bottom pressure can be reduced to about 30 mbar.

Stages III and IV

Before the recycling to absorption stage 1, the solvent stream must be purified to remove acrylic acid substantially, in order to be able to absorb acrylic acid again from the reaction gas of the gas-phase oxidation. The acrylic acid concentration in the solvent stream should not exceed 1, preferably 0.5, % by weight.

The solvent stream obtained in stage (II) may still contain relatively large amounts of acrylic acid, up to about 15% by weight. The reduction in the acrylic acid content of the solvent is effected preferably by stripping with an inert gas or with an inert gas mixture, preferably with a part-stream of the recycled gas or, in the case where propane is the diluent, with propane. The stripping is effected at from about 1.1 to 2.0, preferably from 1.3 to 1.6, bar and at from about 80 to 120° C., preferably from 110 to 120° C. During the stripping, the solvent stream to be purified is fed in at the top of the stripping column; it flows over the baffles toward the bottom. The stripping gas is passed into the bottom of the stripping column and flows countercurrent. While the stripping gas flows toward the top of the column, it absorbs acrylic acid from the liquid solvent stream so that a purified solvent stream which has an acrylic acid concentration of not more than 1, preferably not more than 0.5, % by weight can be taken off from the bottom of the stripping column. This substantially acrylic acid-free solvent can then be recirculated to the absorption stage (I).

The stripping recycled gas laden with acrylic acid is expediently recirculated to the stage in which the partial evaporation of the solvent is effected, or to the absorption column.

The invention is illustrated in more detail below with reference to a figure and with reference to embodiments.

FIG. 1 shows the degree of fouling (DF) expressed in ° C./day in a heat exchanger connected to the bottom of the distillation column as a function of the bottom temperature.

The degree of fouling is a measure of the soiling of the column. It indicates the number of ° C. by which the forward flow temperature of the heat exchange medium in the bottom evaporator must increase per day in order to evaporate a constant amount of bottom product. As shown in the figure, the acrylic acid concentration in the bottom product, which was varied from 0.29% by weight to 4.82% by weight, had no effect on the degree of fouling. Surprisingly, it was found that the degree of fouling is decisively determined by the bottom temperature. The degree of fouling is relatively small and increases only slowly with temperature below 155° C.; it shows an abrupt increase at about 160° C. and increases only moderately with further temperature increase.

EXAMPLES

In a glass column which has a diameter of 30 mm and a height of 3 m and was equipped with 30 dual-flow trays of V4A stainless steel with Teflon seals, a liquid starting mixture having a feed temperature of 50° C. and composed of about 15% by weight of acrylic acid, 0.5% by weight of acetic acid, and 0.1% by weight of water, the remainder being a mixture of biphenyl and dimethyl phthalate in a weight ratio of 80:20, was fed in 8 trays above the bottom. A circulation flash evaporator was connected to the bottom and a quench condenser was connected to the top of the column. The product was drawn off via a side take-off, 5 trays below the top of the column.

For the comparative example, operating conditions closely related to those of the prior art were established:

$p_{top}$=390 mbar, $T_{top}$=105° C., $p_{bottom}$=300 mbar, $T_{bottom}$=185° C., $c_{acrylic\ acid\ in\ the\ bottom\ product}$=2.29% by weight A degree of fouling of 12° C. per day was measured in the circulation flash evaporator.

The following process examples relate to the same experimental arrangement, the operating parameters in each case having been changed according to the data below:

Example 1

$p_{top}$=45 mbar, $T_{top}$=61° C., $p_{bottom}$=50 mbar, $T_{bottom}$=150° C., $c_{acrylic\ acid\ in\ the\ bottom\ product}$=1.61% by weight.

The degree of fouling in the circulation flash evaporator was 4° C. per day.

Example 2

The following operating parameters were established:

$p_{top}$=90 mbar, $T_{top}$=78° C., $p_{bottom}$=100 mbar, $T_{bottom}$=155° C., $c_{acrylic\ acid\ in\ the\ bottom\ product}$=1.21% by weight.

The degree of fouling in the circulation flash evaporator was 4.5° C. per day.

Comparative Example 3

Under the operating conditions, $p_{top}$=90 mbar, $T_{top}$=78° C., $p_{bottom}$=100 mbar, $T_{bottom}$=157.5° C., $c_{acrylic\ acid\ in\ the\ bottom\ product}$=0.83% by weight the degree of fouling in the circulation flash evaporator was 10.2° C. per day.

Comparative Example 4

Under the operating conditions, $p_{top}$=390 mbar, $T_{top}$=105° C., $p_{bottom}$=300 mbar, $T_{bottom}$=165° C., $c_{acrylic\ acid\ in\ the\ bottom\ product}$=4.82% by weight the degree of fouling in the circulation flash evaporator was 12.5° C. per day.

We claim:

1. A process for the continuous recovery of (meth)acrylic acid from the reaction gases containing (meth)acrylic acid and originating from a catalytic gas phase oxidation by
   (I) absorbing the (meth)acrylic acid in a high-boiling organic solvent,
   (II) isolating the (meth)acrylic acid from its mixture with the solvent from
      (I) and, if required, further purifying the (meth)acrylic acid isolated,
   (III) purifying the solvent and
   (IV) recycling the purified solvent to absorption stage (I), wherein the temperature in each process stage does not exceed 155° C. wherein the solvent is purified by stripping with an inert gas.

2. A process as claimed in claim 1, wherein the high-boiling solvent contains biphenyl and diphenyl ether.

3. A process as claimed in claim 2, wherein the high-boiling solvent contains from 0.1 to 25% by weight of dimethyl phthalate.

4. A process as claimed in claim 1, wherein the (meth)acrylic acid is isolated in stage II by evaporation and then further purified by distillation or crystallization.

5. A process as claimed in claim 4, wherein the evaporation is carried out at from 10 to 200 mbar and from 60 to 130° C.

6. A process as claimed in claim 1, in which the (meth)acrylic acid is isolated by distillation from the mixture with the high-boiling solvent, wherein a (meth)acrylic acid concentration of from 5 to 15% by weight is established in the bottom product of the distillation.

7. A process as claimed in claim 1, wherein the inert gas is a part-stream of the recycle gas.

8. A process as claimed in claim 1, wherein said temperature does not exceed 140° C.

9. A process as claimed in claim 8, wherein said temperature does not exceed 120° C.

10. A process as claimed in claim 2, wherein the high-boiling solvent is an azeotropic composition of said biphenyl and diphenyl ether.

11. A process as claimed in claim 10, wherein the high-boiling solvent contains from 0.1 to 25% by weight of dimethyl phthalate.

12. A process as claimed in claim 5, wherein the evaporation is carried out at from 60 to 100 mbar and from 90 to 110° C.

13. A process as claimed in claim 6, wherein said concentration is from 8 to 12% by weight.

* * * * *